US009084809B2

(12) United States Patent
Guerry et al.

(10) Patent No.: US 9,084,809 B2
(45) Date of Patent: Jul. 21, 2015

(54) **IMMUNOGENIC CAPSULE COMPOSITION FOR USE AS A VACCINE COMPONENT AGAINST *CAMPYLOBACTER JEJUNI***

(75) Inventors: Patricia Guerry, Silver Spring, MD (US); Shahida Baqar, Olney, MD (US); Mario Artur Monteiro, Guelph (CA)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/524,057

(22) Filed: Sep. 20, 2006

(65) Prior Publication Data

US 2007/0065461 A1    Mar. 22, 2007

Related U.S. Application Data

(60) Provisional application No. 60/722,086, filed on Sep. 21, 2005.

(51) Int. Cl.
| | |
|---|---|
| *A61K 39/106* | (2006.01) |
| *A61K 31/715* | (2006.01) |
| *A61K 39/385* | (2006.01) |
| *A61K 39/02* | (2006.01) |
| *A61K 47/48* | (2006.01) |
| *A61K 39/00* | (2006.01) |

(52) U.S. Cl.
CPC ............ *A61K 31/715* (2013.01); *A61K 39/105* (2013.01); *A61K 47/4833* (2013.01); *A61K 47/48261* (2013.01); *A61K 2039/6037* (2013.01)

(58) Field of Classification Search
None
See application file for complete search history.

(56) References Cited

U.S. PATENT DOCUMENTS

| | | | | |
|---|---|---|---|---|
| 4,761,283 | A * | 8/1988 | Anderson | 424/194.1 |
| 5,153,312 | A * | 10/1992 | Porro | 530/405 |
| 5,869,066 | A * | 2/1999 | Pace et al. | 424/282.1 |
| 2001/0048929 | A1 * | 12/2001 | Chong et al. | 424/234.1 |

OTHER PUBLICATIONS

Ritter et al Int. J. Cancer 66:184-190, 1996.*
Apsinall et al. Carbohydrate Research 231:13-30, 1992.*
Papp-Szabo et al. Carbohydrate Research vol. 340, 13:2218-2221, Sep. 2005, available online Aug. 1, 2005.*
Baqar et al Vaccine 1995, 13:22-28.*
Roberts. Annu. Rev. Microbiol. 50:285-315.*
Aspinall et al. Carbohydrate Research 231:13-30, 1992.*
Kanipes et al, The Journal of Bacteriology, May 2006, p. 3273-3279.*
Karlyshev et al. Molecular Microbiology Jan. 2005 vol. 55 p. 90-103.*
Ritter et al Int. J. Cancer 66:194-190, 1996.*
Papp-Szabo et al. Carbohydrate Research vol. 340, 13:2218-2221, 2005.*
Aspinall et al. The Journal of Infectious Diseases 1997; 176:s135-8.*
Guerry et al. Infection and Immunity, Feb. 2002, p. 787-793.*
Jennings and Lugowski (The Journal of Immunology, 1981, vol. 127 p. 1011-1018).*
Virtual Chembook—Galactose obtained on Sep. 9, 2008 from http://www.elmhurst.edu/~chm/vchembook/543galactose.html 2 pages.*
Penner et al. Journal of Infectious Diseases, vol. 176, Dec. 1997, p. S135-S138.*
Yun et al. Archives of Pharmacal Research. 2004 vol. 27 (2): 143-150.*
Monteiro et al. Infection and Immunity 2009, 77 (3):1128-1136 Mar. 2009.*
Aspinall, et al. (1994) Biochemistry 33, 241-249.
Aspinall, et al. (1993) Eur. J. Biochem. 213, 1029-1037.
Aspinall, et al. (1995) Eur J. Biochem. 231, 570-578.
St. Michael, et al. (2002) Eur. J. Biochem. 269, 5119-5136.
McNally, et al. (2005) FEBS J. 272, 4407-4422.
Muldoon, et al. (2002) Carbohydrate Res. 337, 2223-2229.
Aspinall, et al. (1992) Carbohydrate Res. 231, 13-30.
Hannify, et al. (1999) Carbohydrate Res. 319, 124-132.

* cited by examiner

*Primary Examiner* — Oluwatosin Ogunbiyi
(74) *Attorney, Agent, or Firm* — Ning Yang; Albert M. Churilla (57) ABSTRACT

An immunogenic composition, and method of using the composition, composed of a capsule polysaccharide polymer from one or more strains *Campylobacter jejuni*. The composition is either used alone or is conjugated to a carrier molecule, such as $CRM_{197}$. An aspect of the invention is that the immunogenic composition induces an immune response without the induction of Gulliam Barre Syndrome.

6 Claims, 5 Drawing Sheets

Strain 81-176 (HS23, 36) CPS    Strain 8486 (HS4, 13, 64, 66) CPS

Strain 81-176 (HS23, 36) CPS-CRM$_{197}$    Strain 8486 (HS4, 13, 64, 66) CPS-CRM$_{197}$

IMMUNOGENIC CAPSULE COMPOSITION FOR USE AS A VACCINE COMPONENT AGAINST CAMPYLOBACTER JEJUNI

CROSS-REFERENCES TO RELATED APPLICATIONS

This application claims priority to U.S. Provisional application 60/722,086, filed Sep. 21, 2005 and is hereby incorporated by reference.

FIELD OF INVENTION

The inventive subject matter relates to an immunogenic composition capable of conferring protection against diarrhea caused by Campylobacter jejuni and a method of inducing an immune response to said composition.

BACKGROUND OF INVENTION

C. jejuni is a leading cause of diarrheal disease worldwide and a documented threat to US military personnel (Taylor, 1992; Tauxe, 1992). The symptoms of campylobacter enteritis include diarrhea, abdominal pain, fever and often accompanied by vomiting. Stools usually contain mucus, fecal leukocytes and blood, although watery diarrhea is also observed (Cover and Blaser 1999). However, despite the importance of this organism to human disease, there are no licensed vaccines against C. jejuni.

Because of the medical importance of C. jejuni, considerable research is dedicated toward understanding this pathogen. However, notwithstanding this effort, there is surprisingly little understanding about how C. jejuni causes human disease. The genome of one strain, NCTC 11168 (Parkhill, et al., 2000) revealed several unusual aspects about the biology of C. jejuni. One striking feature is the presence of an unexpectedly high number of genes encoding putative enzymes involved in sugar and/or polysaccharide synthesis (Parkhill et al., 2000). The sequence, and resulting research fostered primarily by the availability of the sequence, has revealed that these genes fall into 4 main functional clusters that underscore the importance of some unusual carbohydrate structure to the biology of C. jejuni. These clusters include Lipooligosaccharide (LOS) synthesis, genetic control of flagellin glycosylation, genetic control of N-linked glycosylation and the control of the biosynthesis and assembly of capsule.

Vaccine strategies against C. jejuni have been largely limited due to the molecular mimicry between lipooligosaccharide (LOS) cores of many strains of C. jejuni and human gangliosides (Moran, et al., 1996). This mimicry is thought to be a major factor in the strong association of C. jejuni infection with Guillain Barre Syndrome (GBS), a post-infectious polyneuropathy (Allos, 1997). Thus, antibodies generated against LOS cores result in an autoimmune response to human neural tissue. It has been estimated that as many as 1/3000 cases of campylobacter enteritis results in GBS. Therefore, the possibility of developing GBS could be associated with any whole cell vaccine against C. jejuni that includes ganglioside mimicry.

LOS synthesis in Campylobacter is controlled by a number of genes, including genes encoding enzymes involved in biosynthesis of sialic acid for incorporation into LOS. Thus, C. jejuni is one of a limited number of bacteria that can endogenously synthesize sialic acid, a 9 carbon sugar that is found in many mammalian cells. This is consistent with the observed molecular mimicry of LOS and human gangliosides important in GBS (Aspinall et al., 1993, 1994 (a and b); Salloway et al., 1996).

Although glycosylation of proteins was once considered to be a eukaryotic trait, there is an increase awareness of prokaryotic protein glycosylation (Power and Jennings, 2003). The best characterized and most extensively glycosylated bacterial protein is campylobacter flagellin. Flagellin from strain 81-176 is glycosylated at 19 serine or threonine sites by an 0-linkage to pseudaminic acid and derivatives of pseudaminic acid (Thibault et al., 2001). Pseudaminic acid is an unusual 9 carbon sugar that resembles sialic acid, but which is highly immunogenic, unlike sialic acid. Moreover, mutants that are unable to glycosylate flagellin cannot assemble a flagellar filament (Goon et al, 2003). Since flagella are indispensable virulence determinants of C. jejuni, glycosylation is therefore also a key virulence determinant.

One of the most unusual aspects of C. jejuni is the presence of a general system for N-linked glycosylation of numerous proteins (Szymanski et al., 1999; reviewed in Szymanski et al., 2003). This system, which includes an oligosaccharide transferase similar to that found in the eukaryote Saccharomyces cerevisiae, attaches a glycan which has recently been shown to be a heptasaccharide composed of one bacillosamine residue (an unusual deoxy sugar), one D-glucose, and five D-GalNAc residues (Young et al., 2002). The glycosylation appears to occur on numerous periplasmic, and perhaps, surface exposed proteins in C. jejuni (Young et al., 2002). The unusual glycan, again, appears to be highly immunogenic and is recognized during human infection (Szymanski et al., 1999, 2003).

An interesting recent revelation regarding the Campylobacter genome sequence was the presence of a complete set of capsule transport genes similar to those seen in type II/III capsule loci in the Enterobactericeae (Parkhill et al., 2000; Karlyshev et al., 2000). Subsequent genetic studies in which site-specific mutations were made in several capsule transport genes indicated that the capsule was the serodeterminant of the Penner serotyping scheme (Karlyshev et al., 2000; Bacon et al., 2001). The Penner scheme (or HS for heat stable) is one of two major serotyping schemes of campylobacters and was originally thought to be based on lipopolysaccharide O side chains (Moran and Penner, 1999).

Currently it is believed that all of the structures previously described as O side chains are, in fact, capsules. The chemical structures of the capsule/O side chains of several Penner serotypes have been determined, and these structures include several unusual sugar structures, as summarized in Table 1. Thus, the capsule of the genome strain, NCTC 11168, contains a heptopyranose as a L-gluco conformer, which is the first report of such a structure in nature (St. Michael et al., 2002). The capsule of the type strains HS23 and HS36 contain the same carbohydrates in different ratios, and include a mixture of 4 unusual altro-heptoses (6-deoxy-α-D-altro-heptose, D-glycero-α-D-altro-heptose, 6-deoxy-3-Me-α-D-altroheptose, and 3-Me-D-glycero-α-D-altro-heptose (Aspinall et al., 1992).

TABLE 1

Structure of some capsular polysaccharides of *C. jejuni* strains.

| Strain | Structure | Reference |
|---|---|---|
| HS3 | [->4)-α-D-galactose-(1-3)-3 hydroxypropanoyl)-L-α-D-ido-heptose)-(1->)$_n$ | Aspinall et al., 1995 |
| HS19 | β-D-glucuronic acid amidated with 2-amino-2-deoxyglycerol linked to GluNAc | Aspinall et al., 1994 a, b |
| HS23, HS36 | GlcNAc-Gal-D-glycero-α-D-heptose)$_n$, where the D-glycero-α-D-heptose Is a mixture of 4 altro-heptoses | Aspinall et al., 1992 |
| 81116 | Two polysaccharides at a ratio of 3A:1B:A = glucose, glucuronic acid, and mannose that is O-acetylated; B = glucose, galactose, and GlcNAc. | Muldoon et al. (2002) |
| NCTC 11168 | Uronic acid amidated with 2-amino-2-deoxyglycerol at C6 and 6-O-methyl-D-glycero-α-L-gluco-heptopyranose as a side branch. | St. Michael et al. (2002) |

There are several examples of highly effective capsular vaccines. *S. pneumoniae* has 83 different capsular types, but the current *S. pneumoniae* vaccine contains a mixture of the 23 most prevalent serotypes in the US and Europe. *N meningiditis* has fewer serogroups, thus potentially simplifying vaccine development, and, in fact, serogroups A, B and C are responsible for >90% of cases of meningococcal meningitis (Jennings, 1990). However, the polysaccharide from serotype B is poorly immunogenic in man, likely because it mimics human tissues. Capsular vaccines have also been developed against *H. influenzae* and Group B *Streptococcus*.

As previously mentioned, there currently are no licensed vaccines against Campylobacter, due greatly to the molecular mimicry between LOS cores of many strains of *C. jejuni* and human gangliosides (Moran, et al., 1996). However, vaccine formulations incorporating bacterial capsules have been developed against a number of pathogens. In general, capsule vaccines are immunogenic in humans and non-toxic (Jennings, 1990). One of the general problems associated with capsule vaccines is the poor immunogenicity of all polysaccharides in infants, and the fact that many of the capsular vaccines are directed at diseases that are particular threatening to the pediatric population. Based on murine studies, pure polysaccharide antigens are considered to be T cell independent, and capable of inducing only IgM type responses. Adult humans, in contrast, are able to generate IgG, in addition to IgM and IgA antibodies against polysaccharides. Responses in infants to vaccines against type B *H. influenzae* (Schneerson et al 1980; Anderson, 1983; Marburg, 1986), group A, B and C *Neisseria meningiditis* (Jennings and Lugowski, 1981 and 1983; and type 6A *Streptococcus pneumoniae* (Chu et al., 1983) have all improved following conjugation to proteins.

SUMMARY OF INVENTION

Vaccines are the preferred method of conferring anti-diarrhea protection in populations that are potentially exposed to diarrheagenic bacteria. However, currently there are no licensed effective vaccines against *Campylobacter jejuni*.

An object of this invention is an anti-*C. jejuni* immunogenic composition, composed of a capsule polysaccharide polymer, capable of inducing an immune response against important pathogenic strains *C. jejuni* without concomitantly inducing GBS.

Another object of the invention is an anti-*C. jejuni* prophylactic formulation with enhanced T-cell dependent immunity to important pathogenic strains of the bacteria by conjugating the capsule of *C. jejuni* to T-dependent carrier molecules, such as cross reactive material 197 (CRM$_{197}$).

Another object of the invention is a method of administering the carrier conjugated or unconjugated anti-*C. jejuni* capsule polysaccharide composition in order to induce an immune response.

BRIEF DESCRIPTION OF THE DRAWINGS

FIG. 4. Conjugation of (A) *Campylobacter jejuni* strain 81- 176 capsule polysaccharide to carrier protein CRM 197 , and of (B) *Campylobacter jejuni* strain 8486 capsule polysaccharide to carrier protein CRM 197.

DETAILED DESCRIPTION OF PREFERRED EMBODIMENTS

*C. jejuni* capsular moieties are important in serodetermination. However, despite over 60 Penner serotypes having been identified, most Campylobacter diarrheal disease is caused by *C. jejuni* expressing only a limited number of serotypes. Because of the importance of capsule structure in serodetermination, it is postulated that they are highly immunogenic structures. Additionally, they are also unlikely to exhibit the unwanted autoimmune induction caused by immuno-mimicry observed by lipooligosaccharides. Therefore, capsules or capsular components would be highly useful in anti-*C. jejuni* vaccines. *C. jejuni* capsule, as defined in this application, is a generic term for capsular polymers, which are composed of repeating polysaccharide structures. The repeating structures can be homopolymers, defined as a repeating single sugar moiety, or repeating disaccharides or trisaccharides. A number of species of capsular repeating polysaccharide polymers have been identified. To illustrate the genus of capsular polysaccharide structures, Table 2 lists known capsular polysaccharide structures for Campylobacter strains.

The chemical composition of *C. jejuni* capsules were analyzed by first growing *C. jejuni* and then purifying the capsule using water-phenol extraction, ultra-centrifugation and gel permeation chromatography. The specific carbohydrate structures were determined by gas-liquid chromatography (GLC), and GLC-mass spectrometry, and fast atom bombardment-mass spectrometry (FAB-MS). Anomeric configuration of the sugars was determined by nuclear magnetic resonance (NMR) spectrometry.

TABLE 2

| Strain/HS type | Structure | Reference |
| --- | --- | --- |
| HS3 type strain | →4-α-D-Gal-(1→3)(3-hydroxypropanoyl)-L-glycero-α-D-ido-Hep-(1→ | Aspinall et al. (1995) |
| HS19 type strain | →4)-β-D-GlcA-(1→3)-α-D-GlcNAc-(1→<br>(the GlcA units are present as amides of 2-amino-2-deoxyglycerol) | Aspinall et al., 1994 a and b |
| HS23 Type strain and HS 36 Type strain | Four closely-related polysaccharides:<br>→3)-β-D-GlcNAc-(1→3)-α-D-Gal-(1→2)-6d-α-D-altro-Hep-(1→;<br>→3)-β-D-GlcNAc-(1→3)-α-D-Gal-(1→2)-6d-3-O-Me-α-D-altro-Hep-(1→;<br>→3)-β-D-GlcNAc-(1→3)-α-D-Gal-(1→2)-D-glycero-α-D-altro-Hep-(1→;<br>→3)-β-D-GlcNAc-(1→3)-α-D-Gal-(1→2)-3-O-Me-D-glycero-α-D-altro-Hep(1→. | Aspinall et al., 1992 |
| 81116 (HS6) | Two polysaccharides at a ratio of 3A:1B, where<br><br>OAc (30%)           OAc (20%)<br>↓                    ↓<br>3                    6<br>A = →3)-β-D-Glc-(1→2)-α-D-GlcA-(1→3)-α-D-Man-(1→3)-α-D-Glc-(1→<br><br>B = →3)-β-D-GlcNAc-(1→6)-α-D-Glc-(1→4)-α-D-Gal-(1→<br>                                    3<br>                                    ↑<br>                            β-D-GlcNAc-(1 | Muldoon et al. 2002 |
| NCTC 11168 (HS2) | 6-O—Me-D-L-α-L-glc-Hepp-(1<br>↓<br>→2)-β-D-Ribf-(1→5)-β-D-GalfNac-(1→4)-α-D-GlcpA6(NGro)-(1→<br><br>(Here, Glucuronic acid is amidated with 2-amino-2-deoxyglycerol at C-6) | St. Michael et al., 2002 |
| HS41 type strain | Two closely related polysaccharides:<br>→2)-β-L-Araf-(1→2)-β-D-6d-altro-Hepf-(1→2)-β-L-6d-altrof-(1→ (75%); and<br>→2)-β-L-Araf-(1→2)-β-D-6d-altro-Hepf-(1→2)-α-D-Fucf-(1→ (25%) | Hannify et al., 1999 |
| HS30 (C. coli) Type strain | →5-Ribitol-1-P→<br>2<br>↑<br>6d-β-D-talo-Hep-(1→4)-β-D-GlcNAc-(1 | Aspinall et al.1993 |
| HS1 type strain | →4)-β-D-Gal-(1→2)-(R)-Gro-(1-P→<br>(with two branches at C-2 and C-3 of Gal of β-D fructofuranoses that are further substituted at C-3 with O-methyl phosphoramidate groups) | McNally et al., 2005 |
| HS4 (strain 8486) | → -6-d-alpha-D-ido-Hep-(1→4)-beta-D-GlcNAc-(1→ | unpublished |

Based on these analyses, the capsule of C. jejuni strain 81-176 was determined to be a repeating polymer of three carbohydrates, illustrated by the formula: α-D-Gal (1-2)-α-6-deoxy-3-Me-D-altro-heptose (1,3)β-D-acetyl-glucosamine ([→)-α-D-Gal-(1→2)-6d-3-O-Me-α-D-altro Hep-(1→3)-β-D-GlcNAc-(1→]$_n$ ). Position O-2 of Gal unit is partially (approximately 50 to 75%) substituted by O-methylphosphoramidate. Additionally, the capsule of strain CG 8486 was analyzed and shown to be composed of a similar structure but of a repeating disaccharide illustrated by the formula: →3)-6-deoxy-βD-ido-Heptose (1→4)-β-D-GlcNAc-(1→.

Therefore, an aspect of this invention is a vaccine formulation comprised of one or a plurality of species of the genus of capsule polymers of repeating polysaccharides of C. jejuni.

EXAMPLE 1

Immune Response Induced by Anti-C. jejuni Composition Containing C. jejuni Strain 81-176 Capsule In order to demonstrate the immunogenicity of C. jejuni capsule, BALB/c mice were immunized subcutaneously with either phosphate buffer saline (PBS) or purified capsule from C. jejuni 81-176. The ensuing immune reaction was measured by enzyme-linked immunosorbent assay (ELISA) using bovine serum albumin (BSA) as a control. In this analysis, antigen was purified capsule.

In the study, immunization with PBS or 3 doses of 25 µg of capsule did not result in any immune response (secretory IgA in feces, serum IgG or serum IgM).

Immunization with 3 doses of 100 µg or 2 doses of 400 µg of capsule (see below) also resulted in no sIgA response. However, 1/5 animals that received 3 doses of 100 µg showed a serum IgG response (titer of 1:160) and 3/5 animals showed a serum IgM response (titers of 1:4000-1:6000). After 2 doses of 400 µg 3/5 animals had a serum IgG response (titers ranging from 1:640-1:1280) and 5/5 had a serum IgM response (titers ranging from 1:6000-1:10,000). This group did not receive a third immunization due to the strong immune response after only 2 immunizations.

Although the capsule immunogen in this example was administered subcutaneously without adjuvant, subcutaneous administration with adjuvant is contemplated, including but not limited to LTR192G, Aluminum hydroxide, RC529E, QS21, E294, oligodeoxynucleotides (ODN), CpG-containing oligodeoxynucleotides, aluminum phosphate, MPL® (GlaxoSmithKline, Middlesex, UK) or combinations of these or other potential adjuvants. Additionally, although the example illustrates subcutaneous administration, it is also contemplated that administration may be intranasally, with or without adjuvant.

EXAMPLE 2

Immunity to Capsule—$CRM_{197}$ Conjugate

Although significant IgG response was observed in response to purified capsule, in mice, immunity to polysaccharides are often associated with T-cell independent immune responses. Therefore, children are typically only capable of mounting an IgM response in the face of polysaccharide antigens with adults capable of generating an IgG, IgA and IgM response.

Figure 1:
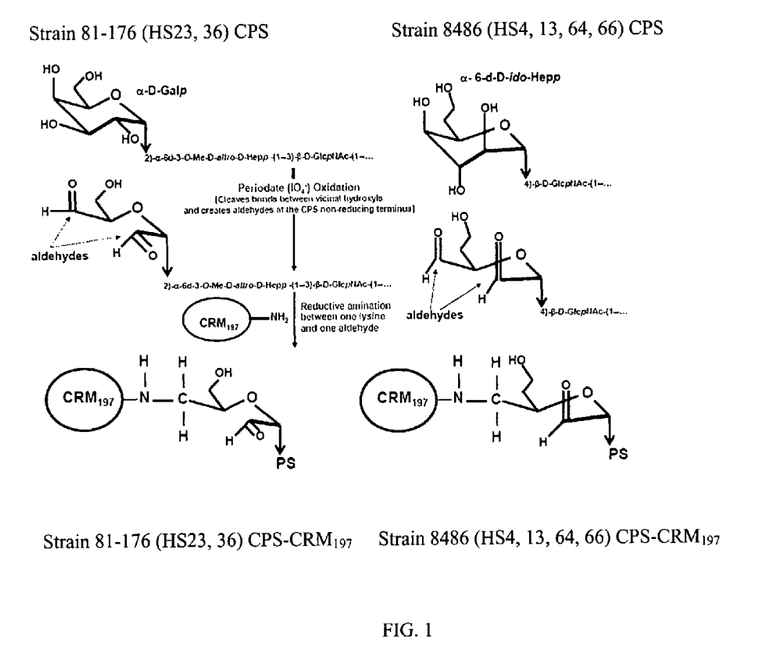
FIG. 1. Schematic diagram showing conjugation of purified capsules of *C. jejuni* strains 81-176 and CG 8486 to CRM$_{197}$. In *C. jejuni* 81-176 capsule, position O-2 of Gal unit is partially (approximately 50-75%) substituted by O-methylphosphoramidate.

In order to potentially further improve the response to capsule moieties, the immunogenicity of C. jejuni capsule was evaluated as a conjugate to T-dependent carrier proteins. A preferred carrier is cross reacting material ($CRM_{197}$), a nontoxic version of diptheria toxin that has been successfully used in pneumococcal conjugate vaccines (Anderson, 1983). Referring to FIG. 1, capsule-CRM conjugate was prepared by oxidizing purified C. jejuni capsule with periodate and covalently linking the oxidized product to CRM at the non-reducing terminus of the CPS (FIG. 1). In FIG. 1, conjugation was conducted on capsule polysaccharide moiety [→3)-α-D-Gal-(1→2)-6d-α-D-altro-Me-Hep-(1→3)-β-D-GlcNAc-(1→]$_n$ or to the polysaccharide moiety α-6-deoxy-ido-Heptose (1→4)-β-GlcNAc.

Immunogenicity of the capsule-CRM conjugate was evaluated in Balb/c mice. Five groups of mice were immunized subcutaneously with 3 doses in 14-day intervals as illustrated in Table 3. Blood was collected on days: −1, 14, 28, 56 and 92. A determination whether the animals had seroconverted to capsule was made by measuring IgM and IgG responses by enzyme-linked immunosorbent assay (ELISA). Endpoint titers for IgM and IgG, shown in FIG. 2, was>56 and>32, respectively. Endpoint titer data is presented as loge. The percent of responding mice to capsule is illustrated in Table 4.

TABLE 3

| Group | Capsule-$CRM_{197}$ (µg) | $CRM_{197}$ (µg) |
|---|---|---|
| A | — | — |
| B | — | 12 |
| C | — | 50 |
| D | 25 | — |
| E | 100 | — |

TABLE 4

| CPS-CRM dose | | % Responders to CPS on study day* | | | | |
|---|---|---|---|---|---|---|
| (µg) | Ig | 14 | 28 | 42 | 56 | 92 |
| 25 | M | 80 | 80 | 80 | 60 | 40 |
|  | G | 0 | 20 | 80 | 80 | 80 |
| 100 | M | 100 | 80 | 100 | 100 | 80 |
|  | G | 0 | 0 | 100 | 20 | 0 |

Figure 2:
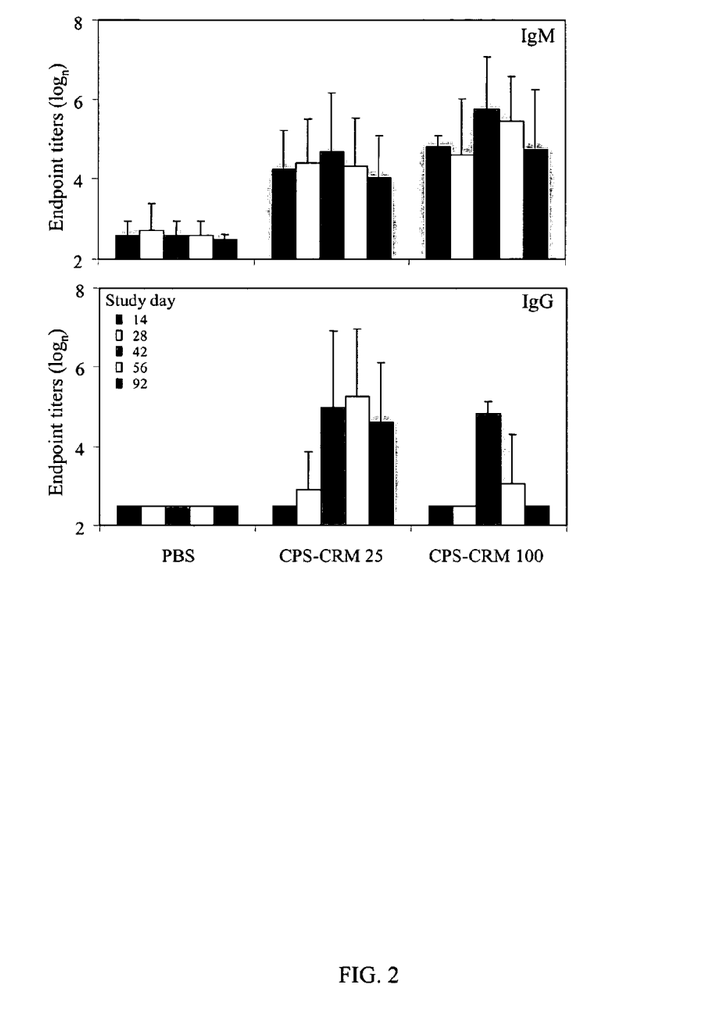
FIG. 2. ELISA results showing antibody response following subcutaneous administration of *C. jejuni* strain 81-176 capsule conjugated to CRM.

As demonstrated in Table 4 and FIG. 2, conjugated capsule induced a strong antibody response to capsule. No seroconversion to capsule was seen in animals receiving phosphate buffered saline only. Although this example illustrates the invention using capsule conjugate from C. jejuni 81-176, the invention also contemplates the use of capsule from other strains of C. jejuni in the production of anti-diarrheal vaccines.

EXAMPLE 3

Longevity of Immune Response in Mice to Capsule-CRM Conjugate

In order to evaluate the longevity of the immune response induced by capsule conjugated to $CRM_{197}$, serum titers were monitored in immunized mice over an extended period. In the study, mice (n=10) were immunized subcutaneously with 3 doses of phosphate buffered saline (PBS)(0), 5, 10, 25 or 50 µg of C. jejuni capsule conjugated to $CRM_{197}$ at 14 day intervals (i.e., study days 0, 14, and 28). Blood samples were collected at intervals before immunization through study day 304 and anti-capsule IgG was determined by enzyme-linked immunosorbent assay (ELISA).

Figure 3:
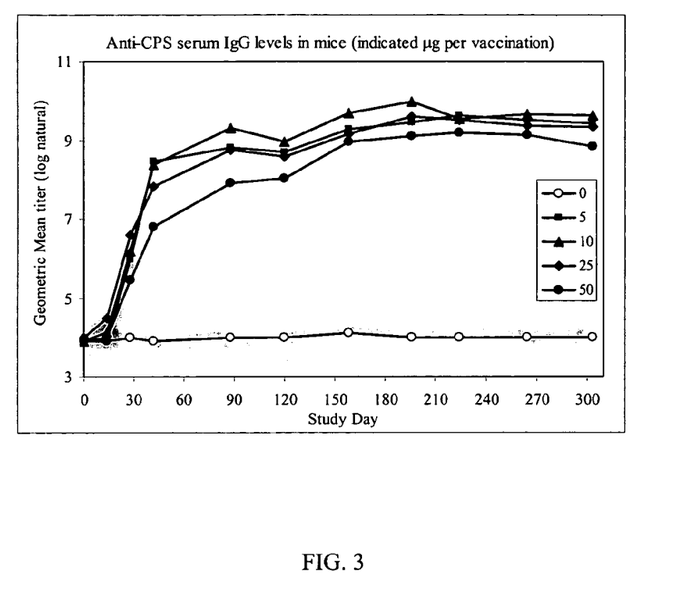
FIG. 3. ELISA results of study illustrating longevity of immune response to capsule conjugated to CRM.

Referring to FIG. 3, in mice immunized with PBS, negligible anti-capsule specific antibodies were detected, which remained unchanged during the course of the study. After 2 doses a low, but easily detectable level, of IgG was detected by ELISA. This response was enhanced following the $3^{rd}$ dose. Although a robust immune response was detected, the study did not yield a discernable vaccine dose response, possibly indicating that dosage levels were initially higher than required. Serum IgG levels peaked at approximately day 90-150 and remained sustained during the experiment. A slight decline in IgG levels was evident after day 196.

EXAMPLE 4

Efficacy of Capsule—CRM Conjugate

Evaluation of the efficacy of C. jejuni capsule—$CRM_{197}$ formulation was evaluated in mice. In this study, mice were immunized with 3 doses of 5, 10 or 25 µg of capsule—$CRM_{197}$ conjugate at 14 day intervals (i.e., days 0, 14 and 28). Control animals received PBS. All animals (n=7) were challenged on day 120, with 4×10$^9$ cfu of C. jejuni 81-176. Following challenge, animals were followed for six consecutive days for the development of infection associated illness. Based on the severity of sickness, a score was assigned to each animal as follows:

0=no apparent illness; 1=ruffled fur;
2=ruffled fur and hunched back; 3=dead.

Daily sickness index and group average indices were calculated. In addition, before challenge and after challenge, loss in body weights were determined. Vaccine efficacy based on illness and loss in body weights was calculated based on the following formula:

$$(control-vaccinated)/(control) \times 100$$

Figure 4:
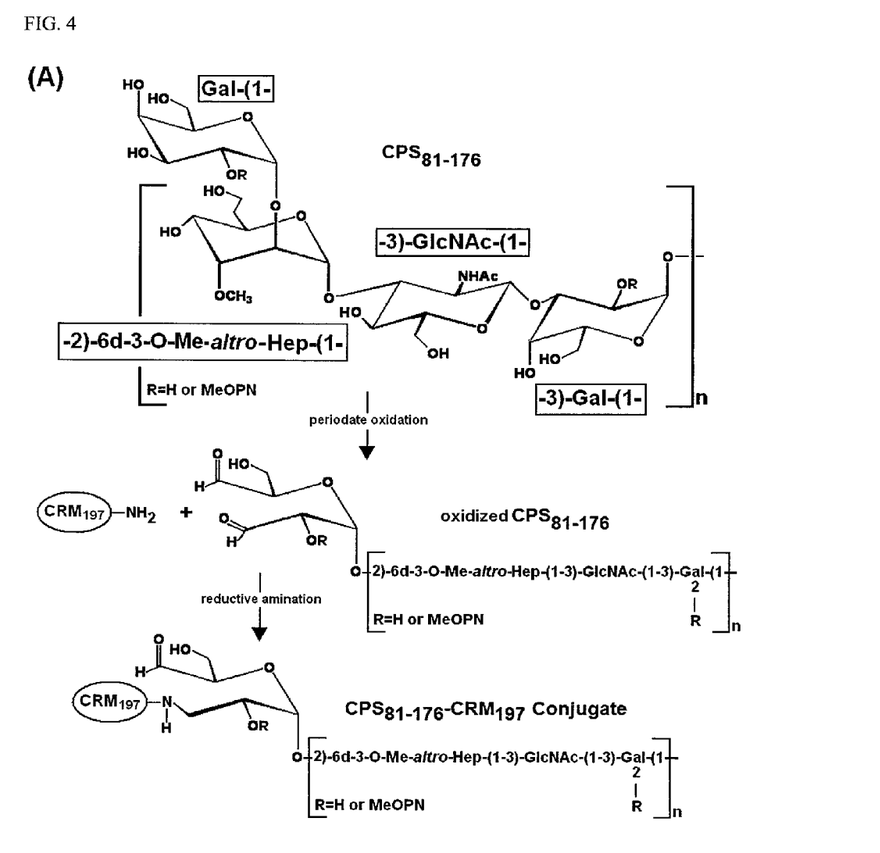
FIG. 4. ELISA results of serum titer of capsule-specific antibody illustrating IgG response in mice protected from challenge by *C. jejuni*.

Referring to FIG. 4, similar capsule-specific serum IgG was seen following immunization with 5, 10 or 25 µg of capsule—$CRM_{197}$. As illustrated in Table 5, a protective immune response was observed with a dose response in terms of protective efficacy. The sickness index was lowest in the group immunized with 25 µg of capsule—$CRM_{197}$ and highest in group immunized with 5 µg of capsule—$CRM_{197}$ conjugate. This dose response was also seen when changes in % body weight were used to evaluate efficacy.

Further characterization of humoral immune responses, capsule-specific serum IgG subclasses (i.e., IgG1, IgG2a and IgG2b) were determined on a limited number of samples. Animals which showed at least 50% protection tended to have higher levels of IgG2b than IgG2a, with a 2b/2a ratio of 4.3+/−1.8 for 9 protected animals and 2.6+/−0.8 for non-protected animals. Higher IgG2b levels are an indication of a Th1 type immune response.

TABLE 5

| CPS_CRM | C. jejuni challenge outcome: | | % efficacy based on: | |
|---|---|---|---|---|
| | | | Sickness | Body |
| µg | Sickness Index | Body weight | Index | weight |
| 0 | 1.19 ± 0.28 | 14.5 ± 5.9 | n/a | n/a |
| 5 | 0.69 ± 0.33 | 10.1 ± 2.9 | 42.1 | 30.3 |
| 10 | 0.73 ± 0.31 | 9.1 ± 4.4 | 38.9 | 37.3 |
| 25 | 0.38 ± 0.19 | 6.6 ± 3.0 | 68.0 | 54.4 |

EXAMPLE 5

Prophetic Example of Induction of Immunity to Capsule in Humans

An aspect of this invention is the ability of *C. jejuni* capsule to induce a vigorous and efficacious immune response in humans but not induction of contraindicating Guillain Barre Syndrome. Optimal methods for inducing protective immunity in humans are preceded by studies in animals such as in mice and monkeys. For each vaccine formulation containing capsules from a single or mixtures of *C. jejuni* strains, a limited amount of experimentation is required to ascertain the optimal effective dose ranges. However, a prophetic method for the induction of anti-*C. jejuni* medicated diarrheal protective immunity contains the following steps:
  a. priming is by administration of an immunogenic formulation containing *C. jejuni* capsule from a single *C. jejuni* or multiple strains of *C. jejuni* bacteria. Alternatively or in addition to purified capsule, the formulation can contain *C. jejuni* capsule conjugated to a T-dependent carrier molecule, such as $CRM_{197}$. The vaccine formulation can be administered orally, nasally, subcutaneously, intradermally, transdermally, transcutaneously intramuscularly, or rectally. Depending on the route of administration, the vaccine formulation can be administered with or without any of a number of adjuvants, including but not limited to LTR 192G, Aluminum hydroxide, RC529E, QS21, E294, oligodeoxynucleotides (ODN), CpG-containing oligodeoxynucleotides, aluminum phosphate, MPL® (GlaxoSmithKline, Middlesex, UK) or combinations of these or other potential adjuvants. The range of a unit dose of immunogen is 0.1 µg to 10 mg of immunogen in a range of buffer solutions.
  b. Subsequent to a priming dose, 2 to 4 boosting doses can also administered with unit dose range of 0.1 µg to 10 mg of immunogen in a buffered aqueous solutions with or without adjuvant.

REFERENCES

1. Allos, B. M. 1997. Association between *Campylobacter* infection and Guillain Barre Syndrome. J. Infect. Dis. 176 (Suppl 2):S125-128.
2. Anderson, P. W. 1983. Antibody responses to *Haemophilus infiuenzae* type b and diptheria toxin induced by conjugates of oligosaccharides of the type b capsule with the non toxic protein $CRM_{197}$. Infect. Immun. 39:233-238.
3. Aspinall, G. O., S. Fujimoto, A. G. MacDonald, H. Pang, L. A. Kuryanczyk and J. L. Penner. 1994a. Lipopolysaccharides from *Campylobacter jejuni* associated with Guillain Barre Syndrome patients mimic human gangliosides in structure. Infect. Immun. 62:2122-2125.
4. Aspinall, G. O., McDonald, A. G., and Pang, H. 1992. Structures of the O chain from lipopolysaccharides of *Campylobacter jejuni* serotypes O:23 and O:36. Carbohyr. Res. 231:13-20.
5. Aspinall, G. O., A. G. MacDonald, H. Pang, L. A. Kuranczyk, and J. L. Penner. 1994b. Lipopolysaccharides of *Campylobacter jejuni* serotype O:19: structures of core oligosaccharide regions from the serostrain and two bacterial isolates from patients with Guillain Barre Syndrome. Biochem. 33:241-249.
6. Aspinall, G. O., A. G. MacDonald, T. S. Raju, H. Pang, L. A. Kuryanczyk, J.L.Penner and A. P. Moran. 1993. Chemical structure of the core region of *Campylobacter jejuni* serotype O:2 lipopolysaccharide. Eur. J. Biochem. 213: 1029-1037.
7. Aspinall, G. O., C. M. Lynch, H. Pang, R. T. Shaver, A. P. Moran. 1995. Chemical structures of the core region of *Campylobacter jejuni* O:3 lipopolysaccharide and an associated polysaccharide. Eur. J. Biochem. 1995. 231(3): 570-578.
8 Baqar, S., Bourgeois, A. L., Applebee, L A., Mourad, A. S., Kleinosky, M. T., Mohran, Z., and J. R. Murphy. 1996. Murine intranasal challenge model for the study of *Campylobacter* pathogenesis and immunity. Infect. Immun. 64:4933-4939.
9. Chu, C., Schneerson, R., Robbins, J. B. and Rastogi, S. C. 1983. Further studies on the immunogenicity of Haemophilus influenzae type b and pneumoccocal type 6A polysaccharide-protein conjugates. Infect. Immun. 40:245-256.
10. Cover, T. L. and M. J. Blaser. 1999. The pathobiology of *Campylobacter* infections in humans. Ann. Rev. Med. 40:269-185.
11. Goon, S., J. F. Kelly, S. M. Logan, C. P. Ewing, P. Guerry. 2003. Pseudaminic acid, the major modification of Campylobacter flagellin, is synthesized via the Cj1293 gene. Mol. Microbiol. 50(2): 659-671.
12. Hanniffy, O. M., A. S. Shashkov, A. P. Moran, M. M. Prendergast, S. N. Senchenkova, Y. A. Knirel, and A. V. Savage. 1999. Chemical structure of a polysaccharide from *Campylobacter jejuni* 176.83 (serotype O:41) containing only furanose sugars. Carbohydr. Res. 319:124-132.
13. Jennings, H. J. Capsular polysaccharides as vaccine candidates. 1990. Curr. Top. Microbiol. Immunol. 150:97-127.
14. Jennings, H. J. and Lugowshi, C. 1981. Immunochemistry of groups A, B and C meningococcal polysaccharides-tetanus toxoid conjugates. J. Immunol. 127:1011-1018.
15. Jennings, H. J., C. W. Lugowski, F. E. Ashton, J. A. Ryan. 1983. The structure of the capsular polysaccharide obtained from a new serogroup (L) of Neisseria meningitidis. Carbohyd. Res. 112(1)::105-111.
16. Karlyshev, A. V., Linton, D., Gregson, N. A., Lastovica, A. J. and Wren, B. W. 2000. Genetic and biochemical evidence of a *Campylobacter jejuni* capsular polysaccharide that accounts for Penner serotype specificity. Mol. Microbiol. 35:529-541.
17. Marburg, S., Jom, D., Tolman, R. L., Arison, B., McCauley, J., Kniskem, P. J., Hagopian, A. and Vella, P. P. 1986. Biomolecular chemistry of macromolecules: synthesis of bacterial polysaccharide conjugates with *Neisseria meningiditis* membrane protein. J. Am. Chem. Soc. 108:5282-5287.
18. McNally, D. J., H. C. Jarrell, J. Li, N. H. Khieu, E. Vinogradov, C. M. Szymanski, and J. R. Brisson. 2005. The HS:1 serostrain of *Campylobacter jejuni* has a complex teichoic acid-like capsular polysaccharide with non-stochiometric fructofuranose branches and O-methyl phosphoramidite groups. FEBS J. 272:4407-4422.
19. Moran, A. P., B. J. Appelmelk, and G. O. Aspinall. 1996. Molecular mimicry of host structures by lipopolysaccharides of *Campylobacter* and *Helicobacter* spp.: implications in pathogenesis. J. Endotox. Res. 3(6):521-531.
20. Moran, A. P. and J. L. Penner. 1999. Serotyping of *Campylobacter jejuni* based on heat-stable antigens: relevance, molecular basis and implications in pathogenesis. J. Appl. Microbiol. 86:361-377.
21. Muldoon, J., A. S. Shashkov, A. P. Moran, J. A. Ferris, S. N. Senchenkova, and A. V. Savage. 2002. Structures of two polysaccharides of *Campylobacter jejuni* 81116. Carbo. Res. 337:2223-2229.
22. Parkhill, J., B. W. Wren, K. Mungall, J. M. Ketley, C. Churcher, D. Basham, T. Chillingworth, R. M. Davies, T. Feltwell, S. Holroyd, K. Jagels, A. V. Karlyshev, S. Moule, M. J. Pallen, C. W. Penn, M. A. Quail, M. A. Rajandream, K. M. Rutherford, A. H. M. van Vliet, S. Whitehead, and B. G. Barrell. 2000. The genome sequence of the food-borne pathogen *Campylobacter jejuni* reveals hypervariable tracts. Nature 403:665-668.
23. Power, P. M. and Jennings, M. P. 2003. The genetics of glycosylation in gram negative bacteria. FEMS Microbiol. Lett. 218:211-222.
24. Russell, R. G., M. J. Blaser, J. I. Sarmiento and J. Fox. 1989. Experimental *Camplobacter jejuni* infectin in Macaca nemestrina. Infect. Immun. 57:1438-1444.
25. Russell, R. G., M. O'Donnoghue, D. C. Jr. Blake, J. Zulty and L. J. DeTolla. 1993. Early colonic damage and invasion of *Camplylobacter jejuni* in experimentally challenged infant Macaca mulatta. J. Infect. Dis. 168:210-215.
26. Salloway, S., L. A. Mermel, M. Seamans, G. O. Aspinall, J. E. Nam Shin, L. A. Kurjanczyk, and J. L. Penner. 1996. Miller Fisher Syndrome associated with *Campylobacter jejuni* bearing lipopolysaccharide molecules that mimic human ganglioside $GD_3$. Infect. Immun. 64:2945-2949.
27. Schneerson, R., Barrera, O., Sutton, A. and Robbins, J. B. 1980. Preparation, characterization and immunogenicity of Haemophilus influenzae type b polysaccharide protein conjugates. J. Exp. Med. 152:361-376.
28. St. Michael, F., C. M. Szymanski, J. Li, K. H. Chan, N. H.Khieu, S. Larocque, W. W. Wakarchuk, J. -R. Brisson, and M. A. Monteiro. 2002. The structures of the lipooligosaccharide and capsule polysaccharide of *Campylobacter jejuni* genome sequenced strain NCTC 11168. Eur. J. Biochem. 269:5119-5136.
29. Szymanski, C. M., Yao, R., Ewing, C. P., Trust, T. J., and Guerry, P. (1999) Evidence for a system of general protein glycosylation in *Campylobacter jejuni*. Mol Microbiol 32: 1022-1030.
30. Szymanski, C. M., Logan, S. M., Linton, D., and Wren, B. W. 2003. *Campylobacter*-a tale of two protein glycosylation systems. Trends Microbiol. 11:233 238.
31. Tauxe, R. V. (1992) Epidemiology of *Campylobacter jejuni* infections in the United States and other industrialized nations. In *Campylobacter jejuni: Current status and future trends* (Edited by Nachamkin I., Blaser M. J. and Tompkins L. S.), p. 9. American Society for Microbiology, Washington, D.C..
32. Taylor, D. N. (1992) Campylobacter infections in developing countries. In *Campylobacter jejuni: Current status and future trends* (Edited by Nachamkin I., Blaser M. J. and Tompkins L. S.), p. 20. American Society for Microbiology, Washington, D.C..
33. Thibault, P., Logan, S. M., Kelly, J. F., Brisson, J. -R., Ewing, C. P., Trust, T. J., and Guerry, P. (2001) Identification of the carbohydrate moieties and glycosylation motifs in *Campylobacter jejuni* flagellin. J Biol Chem 276: 34862-34870.
34. Young, N. M., Brisson, J. -R., Kelly, J., Watson, D. C., Tessier, L., Lanthier, P. H., Jarrell, H. C., Cadotte, N., St. Michael, F., Aberg, E., and Szymanski, C. M. 2002. Structure of the N linked glycan present on multiple glycoproteins in the gram negative bacterium, *Campylobacter jejuni*. J. Biol. Chem. 277:42530-42539.

What is claimed is:

1. An immunogenic composition, composed of isolated *Campylobacter jejuni* capsule polysaccharide polymer comprising a repeating trisaccharide structure having the formula [→3)-α-D-Gal-(1→2)-6d-3-O-Me-α-D-altro-Hep-(1→3)-β-D-GlcNAc-(1→], wherein the non-reducing terminus of said capsule polysaccharide polymer is said galactose, and wherein said galactose non-reducing terminus is directly conjugated to a protein carrier molecule.

2. The immunogenic composition of claim 1, wherein said protein carrier molecule is cross reactive material 197 ($CRM_{197}$).

3. The immunogenic composition of claim 2, wherein said carrier molecule is conjugated by reductive animation.

4. The immunogenic composition of claim 1, wherein said repeating trisaccharide structure contains O-methyl-phosphoramidate at the O-2 position of Gal.

5. A method of producing anti-*Campylobacter jejuni* immunity comprising the steps:
   a. administering the immunogenic composition of claim 1 with or without adjuvant at a dose range of 0.1 μg to 10 mg per dose;
   b. administering a boosting dose of said immunogenic composition with or without adjuvant at a dose range of 0.1 μg to 10 mg per dose.

6. The method of claim 5, wherein said protein carrier is $CRM_{197}$.

* * * * *